United States Patent [19]
Trerotola et al.

[11] Patent Number: 5,591,226
[45] Date of Patent: Jan. 7, 1997

[54] PERCUTANEOUS STENT-GRAFT AND METHOD FOR DELIVERY THEREOF

[75] Inventors: Scott O. Trerotola, Carmel, Ind.; Wade M. Johnson, Minneapolis, Minn.

[73] Assignees: Schneider (USA) Inc., Plymouth, Minn.; Indiana University Foundation, Bloomington, Ind.; Johns Hopkins University, Baltimore, Md.

[21] Appl. No.: 377,069

[22] Filed: Jan. 23, 1995

[51] Int. Cl.$^6$ ............................. A61F 2/06; A61F 11/00
[52] U.S. Cl. .................... 623/1; 623/12; 606/108
[58] Field of Search ................ 623/1, 12; 606/108, 606/191, 195, 198; 604/96, 103, 104

[56] References Cited

U.S. PATENT DOCUMENTS

| | | | |
|---|---|---|---|
| 4,487,567 | 12/1984 | Possis et al. | 425/403 |
| 4,546,499 | 10/1985 | Possis et al. | 623/1 |
| 4,562,597 | 1/1986 | Possis et al. | 623/1 |
| 4,601,718 | 7/1986 | Possis et al. | 623/1 |
| 4,655,771 | 4/1987 | Wallsten | 623/1 |
| 4,804,382 | 2/1989 | Turina | 623/1 |
| 4,848,343 | 7/1989 | Wallsten et al. | 128/343 |
| 4,850,999 | 7/1989 | Planck | 623/1 |
| 4,909,979 | 3/1990 | Possis et al. | 264/571 |
| 4,950,227 | 8/1990 | Savin | 604/8 |
| 5,061,275 | 10/1991 | Wallsten et al. | 623/1 |
| 5,064,435 | 11/1991 | Porter | 623/12 |
| 5,071,407 | 12/1991 | Termin et al. | 604/104 |
| 5,158,545 | 10/1992 | Trudell | 604/53 |
| 5,246,452 | 9/1993 | Sinnott | 623/1 |
| 5,389,106 | 2/1995 | Tower | 606/198 |
| 5,403,341 | 4/1995 | Solar | 606/198 |

FOREIGN PATENT DOCUMENTS

| | | |
|---|---|---|
| 0485133 | 5/1992 | European Pat. Off. . |
| 9308768 | 5/1993 | WIPO . |
| 17636 | 9/1993 | WIPO ............................. 623/1 |
| 9514442 | 11/1994 | WIPO . |

OTHER PUBLICATIONS

"Cannulation of Blood Vessels for Prolonged Hemodialysis", Wayne Quinton, David Dillard and Belding H. Scribner, ASAIO Trans., p. 104 (1960).

"Experimental Study of Stent Graft Placement for Treatment of Aneurysms in the Canine Aorta —Final Report (abstract)", B. Hagen, MD, Radiological Department, Martin–Luther–Krankenhaus, Berlin, Germany, Cardiovasc Intervent Radiol, 17 (Supp.2), p. S49 (1994).

"Thrombectomy Below the Inguinal Ligament with the Hydro–Lyser Catheter (abstract)", J. A. Reekers; J. G.Kromhout; J. H. Spithoven. Dept. Radiology and Vasc. surg Academic medical centre Amsterdam, Comm. Hosp. Doetinchem, Cardiovasc Intervent Radiol, 17 (Supp. 2), p. S49 (1994).

"Puncturing of Incorporated Vascular Stents —An Experimental Study (abstract)", K. Schurmann; D. Vorwerk; C. Rosenbaum; A. Kulisch; S. Mechmann; and R. W. Gunther. Diagnostic Radiology and Cardiovascular Surgery, University of Technology Aachen, Germany, Cardiovasc Intervent Radiol; 17 (Supp. 2), p. S49 (1994).

"A New Type Wall Stent in Superior Vena Cava Stenting (abstract)", M. Oudkerk; O. Loosveld; R. de Wit; and Dr. Daniel den Hoed Center, Rotterdam, Netherlands, Cardiovasc Intervent Radiol; 17 (Supp. 2), p. S49 (1994).

"Percutaneous Femoropopliteal Graft Placement", Andrew H. Cragg, MD and Michael D. Dake, MD, Radiology 187, pp. 643–648 (1993).

(List continued on next page.)

Primary Examiner—Michael J. Milano
Attorney, Agent, or Firm—Haugen and Nikolai, P.A.

[57] ABSTRACT

A percutaneous stent-graft is disclosed for restoring blood flow between vessels. The stent-graft has a body implantable device and first and second peel-away retaining elements. Also disclosed are methods for deploying a stent-graft.

17 Claims, 10 Drawing Sheets

OTHER PUBLICATIONS

"Transfemoral Endovascular Stented Graft Treatment of Aorto–liiac and Femoropopliteal Occlusive Disease for Limb Salvage", Michael L. Marin, MD; Frank J. Veith, MD; Jacob Cynamon, MD; Luis A. Sanchez, MD; Kurt R. Wengerter, MD; Michael L. Schwartz, MD; New York, New York, Juan C. Parodi, MD; Buenos Aires, Argentina, Thomas F. Panetta, MD, Curtis W. Bakal, MD; William D. Suggs, MD; New York, New York, Am. J. Surg. 168: pp. 156–162 (1994).

"Comparison of Gianturco Z Stents and Wallstents in a Hemodialysis Access Graft Animal Model", Scott O. Trerotola, MD; Jeffrey H. Fair, MD; Darrell Davidson, MD, Ph.D; Michael A. Samphilip, Jr., BS; Carolyn A. Magee, JUIR(1993).

"Gianturco Self–Expanding Stent in the Treatment of Stenosis in Dialysis Access Grafts", Gerald A. Beathard, Kidney International; 43:872–877 (1993).

"Follow–up Results After Stent Placement in Failing Arteriovenous Shunts: A Three–Year Experience", D. Vorwek; R. W. Gunther; K. Bohndorf; D. Kistler; U. Gladziwa; and H. G. Sieberth. Department of Diagnostic Radiology, Technical University of Aachen, Germany, Cardiovasc Intervent Radiol; 14:285–289 (1991).

"Venous Stenoses in Patients Who Undergo Hemodialysis: Treatment with Self–Expandable Endovascular Stents", Stephen F. Quinn, MD; Earl S. Schuman, MD; Lee Hall, MC, Comdr, USMC; George F. Gross, MD; Barry T. Uchida, BA; Blayne A. Standage, MD; Joseph Rosch, MD; Krasnodar Ivancev, MD, Radiology; 183:499–504 (1992).

"Use of the Wallstent in the Venous System Including Hemodialysis–Related Stenoses", Christoph L. Zollikofer; Francesco Antonucci; Gerd Stuckmann; Paul Mattias; Werner F. Bruhlmann; and Erich K. Salomonowitz. Department of Radiology, Kantonsspital Winterhur, Winterhur, Switzerland, and Department of Radiology, Stadtspital Triemli, Zurich, Switzerland, Cardiovasc Intervent Radiol; 15:334–341 (1992).

"Salvage of Angioaccess after Late Thrombosis of Radiocephalic Fistulas for Hemodialysis", Arturo Romero, MD; Jose R. Polo, MD; Eugenio Garcia Morato, MD; Jose L. Garcia Sabrido, MD; Antonio Quintans, MD; and Julio P. Ferreiroa, MD, Int. Surg.; 71:122–124 (1986).

"Nine Years' Experience with Internal Arteriovenous Fistulas for Haemodialysis: A Study of Some Factors Influencing the Results", P. Kinnaert; P. Vereerstraeten; C. Toussaint; and J. Van Geertruyden, Br. J. Surg. 64:242–246 (1977).

"Permanent Vascular Access: A Nephrologist's View", David W. Windus, MD., Am. J. Kid. Dis., vol. 21, No. 5, pp. 457–471 (May 1993).

"Hemodialysis Graft Salvage", David N. Brotman, MD; Luis Fandos, MD; Glenn R. Faust, MD; William Doscher, MD, FACS; and Jon R. Cohen, MD, FACS, J. Am. Coll. Surg.; 178:431–434 (1994).

"Extended Patency of Expanded Polytetrafluoroethylene Grafts for Vascular Access Using Optimal Configuration and Revisions", Richard P. Rizzuti, MD; John C. Hale, MD, FACS; and Thomas E. Burkart, MD, Surg. Gyn & Ob, 166:23–27 (1988).

"Vascular Access for Hemodialysis", Steven B. Palder, MD; Robert L. Kirkman, MD; Anthony D. Whittemore, MD; Raymond M. Hakim, MD; J. Michael L. Lazarus, MD; and Nicholas L. Tilney, MD, Ann. Surg., pp. 235–239 (1985).

"Salvage Operations For Malfunctioning Polytetrafluoroetylene Hemodialysis Access Grafts", Edward E. Etheredge, MD, Ph.D.; Stephen D. Haid, BA; Marge N. Maeser, RN; Gregorio A. Sicard, MD; and Charles B. Anderson, MD, Surgery; 94(3):464–470 (1983).

F–D–C Reports, Inc., *Bard Will Market Possis' Perma–Seal Dialysis Access Graft*, Jan. 9, 1995.

PERCUTANEOUS STENT-GRAFT AND METHOD FOR DELIVERY THEREOF

BACKGROUND OF THE INVENTION

Over 130,000 patients undergo chronic hemodialysis in the United States each year. Access to the blood supply is generally sought through vasculature, but such access may eventually fail due to the formation of scar tissue inside the vessel or due to vessel occlusion. Failure of hemodialysis access contributes to morbidity, hospitalization time, and the cost of treatment.

It is known in the art to regain vessel access with new hemodialysis grafts and hemodialysis graft revisions which are performed surgically. The Brescia-Cimino direct radiocephalic fistula is a preferred form of permanent access, but access is generally regained by implanting bridge grafts. The majority of such grafts in the United States are made of synthetic graft material such as PTFE. Unfortunately, PTFE bridge grafts are much more prone to stenosis and thrombosis than the natural vessels.

While percutaneous interventional techniques (such as thrombolysis, angioplasty, atherectomy, and stent placement) are becoming increasingly popular in the management of hemodialysis access graft complications, these techniques generally eventually fail, necessitating surgical revision. Such revision usually consists of the implanting of a PTFE interposition graft, and offer 30-day patencies of about 44–65%. Occasionally, the interposition grafts do not fully span the diseased segment due to lack of imaging guidance. Surgical revision of these lesions may entail patch angioplasty or placement of an interposition graft.

PTFE interposition grafts are also often placed in patients who have a failed native fistula. Usually, these fistulae retain a small segment of patent vein beyond the anastomosis, and have reconstitution of veins further up the arm via collaterals. This segment of vein is used to form an arterial anastomosis of the interposition graft.

The advent of covered stents and stent-grafts has made possible the revascularization of long segment occlusion in the arterial system. To date, however, such grafts have been used intravascularly. In other words, the grafts have been inserted inside of natural veins or arteries. The ends of these grafts are generally held in place by stents which are either attached to or incorporated into the graft itself, creating "sutureless anastomoses".

It is an object of the present invention to provide extravascular revision and de novo creation of arteriovenous shunts for hemodialysis and other applications. In particular, it is an object of the present invention to provide a percutaneous stent-graft and a method for delivery thereof to provide increased vascular flow in patients requiring the same.

It is a further object of the present invention to provide methods for using percutaneous stent-grafts in a variety of medical applications, such as femoropoplitial, femorals, iliacs, femoral-femoral, brachial-axillary, and forearm loops. These applications include arterial-arterial, venous-venous, arterio-venous, and graft to vessel applications.

SUMMARY OF THE INVENTION

These and other objects are achieved by the apparatus and methods of the present invention. The present invention relates to percutaneous creation of "anastomoses" and the performance thereof in an extraanatomic fashion to create an arteriovenous shunt. The technique is relatively simple and effective. Preferred use of peel-away sheaths circumvents a problem with the insertion of extraanatomic grafts; namely one has to "give up" both ends of the device at some point, so over-the-wire insertion is not possible. Tandem peel-away sheaths represent a simple, effective means of insertion of both ends of the graft into their respective vessels.

In sum, the present invention relates to an apparatus for providing access to a blood supply. The apparatus has a body implantable device made of a flexible tube of open weave construction having a first end and a second end, the ends being compressible into radially compressed states, the flexible tube having an elastic layer arranged along at least a portion of its length, and first and second removable retaining elements secured to the flexible tube proximate the first and second ends, respectively, for maintaining the first and second ends in radially compressed states, the retaining elements being adapted for insertion into vascular access means. The removable retaining elements may be peel-away sheaths, which may be a tubular material attached to at least two leaves, the leaves upon an application of force being adapted to tear the tubular material thereby separating the sheath into removable pieces. The leaves may have handles to facilitate the application of the force. The flexible tube may be constructed of helical, braided strands of biocompatible material, such as stainless steel, Elgiloy, Nitinol, combinations thereof, or plastic. The elastic layer may cover at least part of the internal or external surface of the flexible tube, or the elastic layer may at least partially embed the flexible tube. The elastic layer may be a semi-permeable biostable material such as polytetrafluoroethylene, polyester, polyurethane, or silicone. The flexible tube may be self-expanding, and the ends may be elastically compressible.

The present invention also relates to a system for delivering a percutaneous stent-graft. The system includes a) a body implantable device made of a flexible tube member of open weave construction having a first end and a second end, the ends being compressible into radially compressed states, the flexible tube having an elastic layer disposed along at least a portion of its length; b) first and second removable retaining elements secured to the flexible tube proximate the first and second ends, respectively, for maintaining the first and second ends in radially compressed states wherein the retaining elements are adapted for insertion into vascular access means; and c) first and second vascular access means adapted to receive the first and second removable retaining elements, respectively.

The present invention also relates to a method for delivering a percutaneous stent graft to a patient. The method includes a) creating two incisions and tunneling between the two incisions below skin level to create a percutaneous, extravascular lumen; b) inserting a stent graft into the percutaneous, extravascular lumen, wherein the stent-graft has a first end and a second end, the first end being placed into one of the incisions and the stent graft being pushed until it is disposed in large part within the percutaneous, extravascular lumen, and c) inserting the first end of the stent-graft into a first vascular segment and the second end of the stent graft into a second vascular segment to create a percutaneous, extravascular lumen for allowing blood flow.

The present invention also relates to a method for delivering a percutaneous stent-graft to a patient including a) inserting a first vascular access means into a first body lumen section of the patient; b) inserting a second vascular access means into a second body lumen section of the patient; c) providing an apparatus having body implantable device made of a self-expanding flexible tube of open weave construction having a first end and a second end, the ends being compressible into a radially compressed state, the flexible tube having an elastic layer arranged along at least a portion of its length, first and second removable retaining elements secured to the flexible tube proximate the first and second ends, respectively, for maintaining the first and second ends in radially compressed states, the retaining elements being adapted for insertion into the first and second vascular access means; d) inserting the first and second removable retaining elements into the first and second vascular access means, respectively; e) pushing the first and second removable retaining elements into the first and second vascular access means, respectively, until at least part of the flexible tube first end is disposed within the first body lumen and at least part of the flexible tube second end is disposed within the second body lumen; f) removing the first and second vascular access means; and g) removing the first and second retaining means thereby allowing the first and second end sections to expand within the first and second body lumen sections, respectively. The method may further include the step of tunnelling between two incisions to create a percutaneous path for the stent-graft. The body implantable device may have at least one barb configured for engaging the internal surface of the first and second vessel segments.

BRIEF DESCRIPTION OF THE DRAWINGS

The following figures have been provided to illustrate, but not limit, the present invention.

DESCRIPTION OF THE PREFERRED EMBODIMENTS

Figure 1:
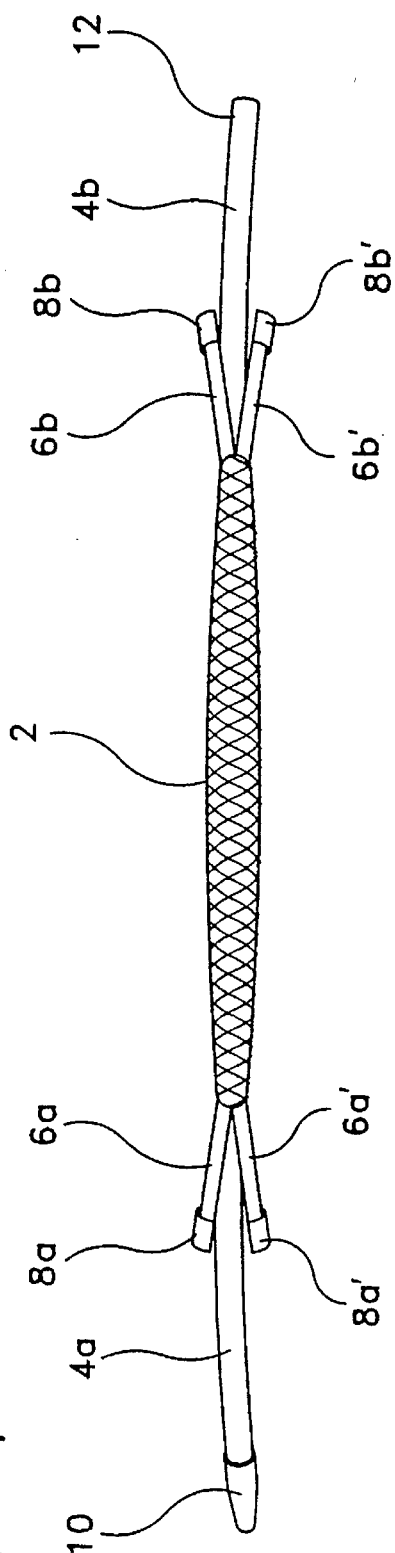
FIG. 1 is a side elevational view of the percutaneous stent-graft of the present invention.

FIG. 1 illustrates a percutaneous stent-graft of the present invention. A body implantable device 2 consists of a stent-graft, in this case a self-expanding flexible tube member of open weave construction covered by an elastic layer. In alternative embodiments, the tube member will not be self-expanding. On each end are removable retaining elements 4a,b. The flexible tube 2 lies in part within each removable retaining means 4a,b in a compressed state. When the retaining means 4a,b are removed in this embodiment, the flexible tube ends will self expand under an elastic restoring force. In alternative embodiments, the ends can be expanded by other means, such as by a balloon. The removable retaining means 4a,b in this case are peel-away sheaths having leaves 6 a,a',b,b' and handles 8 a,a',b,b'. A removable tip 10 is shown on one of two releasable retaining means. The tip 10 is capable of sealing-off blood flow through the stent-graft after end 12 is inserted, but tip 10 is removed prior to insertion into vascular access means 26a,b shown in FIGS. 4(a)–4(i). End 12 will generally be configured for slidable insertion into vascular access means, as will be the end within tip 10.

The stent-graft of the present invention may include a flexible tube such as stents that are known in the art. See, for instance, U.S. Pat. Nos. 4,655,771; 4,848,343; 4,850,999; 5,061,275; and 5,064,435. (All documents cited herein, including the foregoing, are incorporated herein in their entireties for all purposes.) The stents will preferably be self-expanding, however balloon expandable stents may be used under certain circumstances.

The elastic layer will preferably cover the flexible tube at least in part, but it may also be configured inside of the flexible tube at least in part, or it may embed the filaments of the flexible tube at least in part. Elastic layers used in grafts and covered stents that are known in the art are generally suitable for use in the present invention. Preferred elastic layers are made from PTFE or polyurethane. Alternatively, polyester weaves or silicone can be used. Silicone layers may be electrostatically spun.

Figure 2:
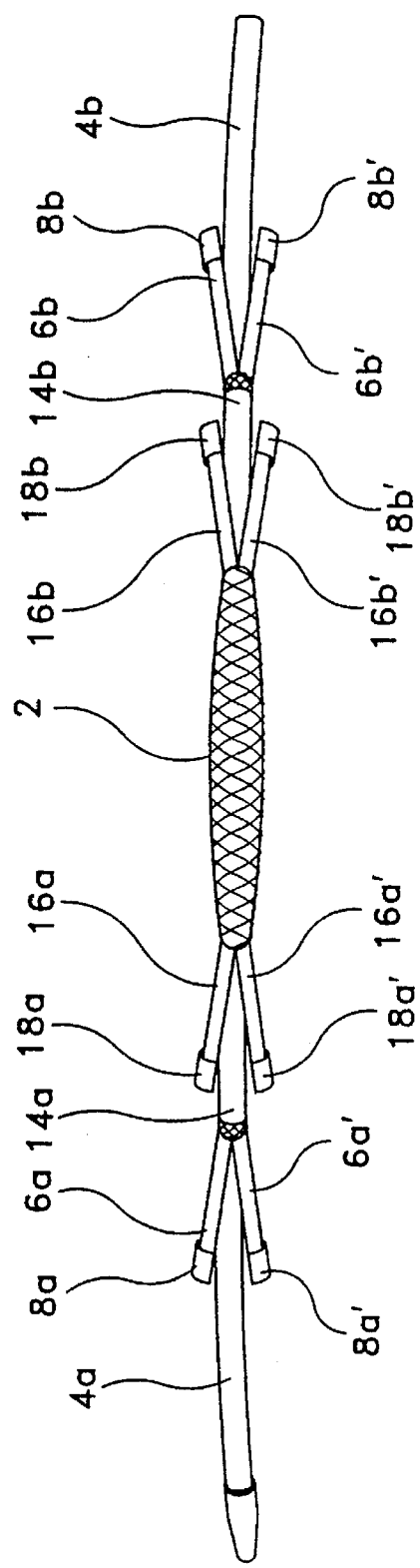
FIG. 2 is a side elevational view showing a percutaneous stent-graft of this invention with gripping means.

FIG. 2 shows a percutaneous stent-graft of the present invention with gripping means 14a,b. The gripping means 14a,b allow the stent-graft to be handled, and especially inserted into the vascular access means, without damaging the flexible tube member 2. In the embodiment shown, gripping means 14a,b is a peel-away sheath having leaves 16a,a',b,b' and handles 18a,a',b,b'. In this embodiment, two gripping means 14a,b are shown, each configured between exposed tube member 2 and removable retaining elements 4a,b. In other embodiments, there will be, for instance, a single gripping means 14 configured between removable retaining means 4a,b.

Figure 3C:
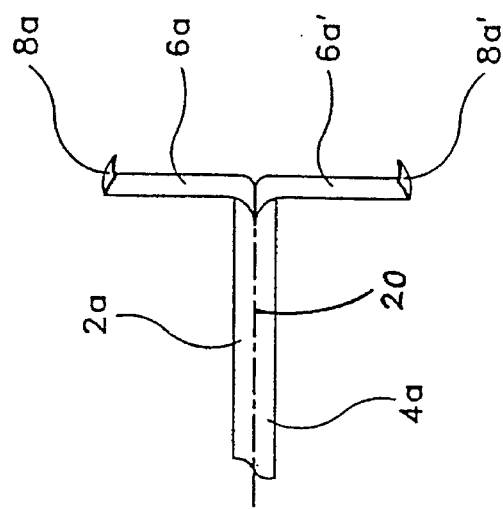
FIGS. 3(a)–3(c) are side elevational views showing peel-away sheaths of the present invention.
Figure 3B:
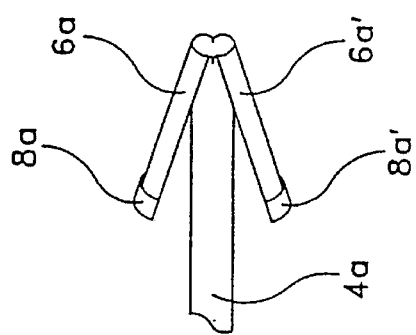
Figure 3A:
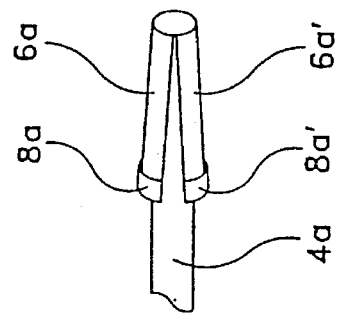

FIGS. 3(a)–3(c) show a method by which removable retaining element 4a,b, gripping means 14a,b (FIG. 2), or vascular access means 26a,b (FIGS. 4(a)–4(i) can be removed. Reference is made in the figures to removable retaining elements 4a,b, but the principle is equally applicable to gripping means 14a,b (FIG. 2) or vascular access means 26a,b (FIGS. 4(a)–4(i). As shown in FIG. 3(a), the leaves 6a,a' and handles 8a,a' will generally lie against the tubular outer surface of the retaining means 4a to maintain a low profile FIG. 3(b) demonstrates that, in some cases, leaves 6a,a' will begin to open after ends 12 are inserted into vascular access means 26a,b (FIGS. 4(a)–4(b)). As shown in FIG. 3(c), the handles 8a,a' can be grabbed by finger tips or by a hemostat, and then pulled so that the handles 8a,a' and leaves 6a,a' are pulled from the tubular body of the retaining means 4a. A continued pulling force can then be exerted against handles 8a,a' or leaves 6a,a' in generally opposite directions, creating a tear along line 20. Continued pulling force will tear the tubular body of the retaining means 4a along its entire length creating separated pieces, which can then be removed.

Alternative retaining elements that can be used pursuant to this invention include clasps that can be opened for removal, or adhesive strips that can be separated for removal.

FIGS. 4(a)–4(i) illustrate a method for deploying the stent-graft of the present invention. Vascular access means 26a,b are inserted into a first vascular segment 22 and a second vascular segment 24, respectively (FIG. 4(a)). The vascular access means 26a,b in this case are peel-away sheaths with leaves 28 a,a',b,b' and handles 30 a,a',b,b'. The distal ends of the vascular access means 26a,b are tubular and adapted to puncture the vascular segments to gain access thereto. Incisions 32a,b are made to provide access for a tunneling means 34 (4(b)). Vascular access means 26a,b are placed within the incision opening. Tunnel means 34, in this case a peel-away sheath/dilator system, is then pushed into one incision and out the other incision so that it is situated under the skin. A first retaining element 4a is inserted through incision 32b into tunnel means 34 and pushed until first retaining element 4a exits incision 32a, at which point first retaining element 4a is inserted into the first vascular access means 26a (FIG. 4 (c)). As first retaining element 4a is pushed into first vascular access means 26a, leaves 6a,a' open up to a partially open position. The peel-away tunnel 34 is removed by pulling leaves 36a,b, thereby tearing tunnel 34 along its entire length, and then removing the pieces. (FIG. 4(d)). First vascular access means 26a is then peeled-away while ensuring that first retaining element 4a means does not materially alter its position (FIG. 4(e)). First retaining element 4a is then peeled-away, thereby deploying a first end 40 of the stent-graft into the first vessel segment 22 (FIG. 4(f)). The stent-graft is deployed in first vessel segment 22. (FIG. 4(g)). Second retaining element 4b is then inserted into second vascular access means 26b (FIG. 4(h)). Second vascular access means 26b and then second retaining element 4b are then removed, deploying a second end 42 of the stent-graft in the second vessel segment 24 (FIG. 4(i)).

The peel-away sheaths of the present invention can generally be removed by peeling and removing, or they may be removed with a combined peeling/sliding action. For instance, retaining means 4a can be slid partially away from first vascular segment 22 while substantially maintaining the position of the stent graft 2; then retaining means 4a can be partially peeled; then retaining means 4a can be slid further from the first vascular segment 22; then retaining means 4a can be further peeled, etc, until retaining means 4a separates and is then removed. Similar sliding/peeling methods of removal can be used with the gripping means 14a,b (FIG. 2), vascular access means 26a,b (FIGS. 4(a)–4(i), and tunnel means 34 (FIGS. 4(b)–4(d)).

Figure 4A:
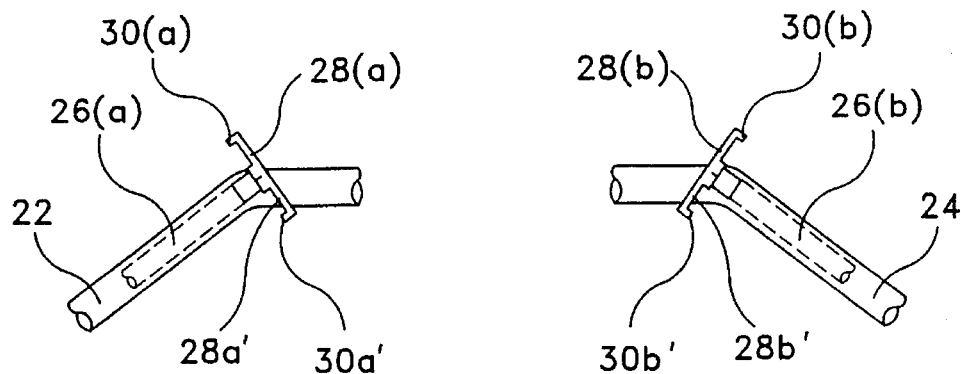
FIGS. 4(a)–4(i) illustrate a method for delivering a percutaneous stent-graft of the present invention.
Figure 4B:
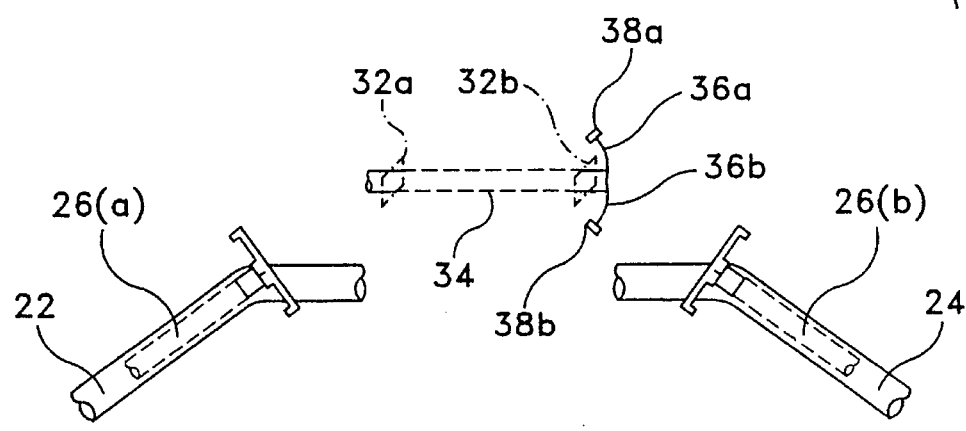
Figure 4C:
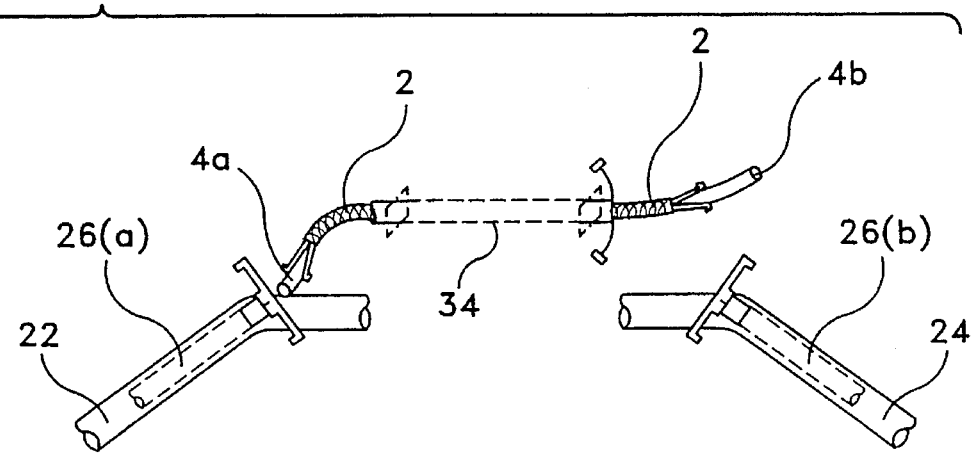
Figure 4D:
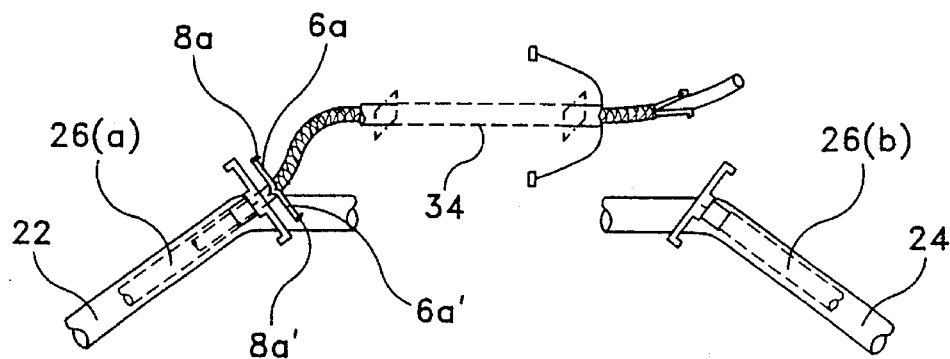
Figure 4E:
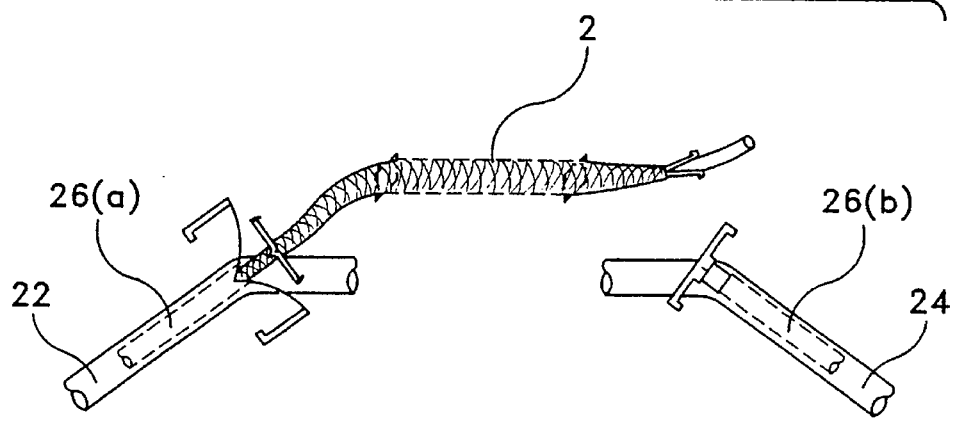
Figure 4F:
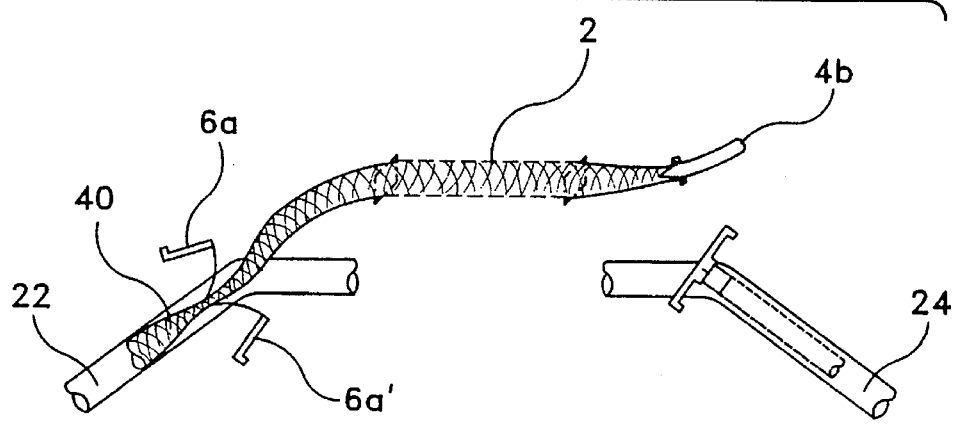
Figure 4G:
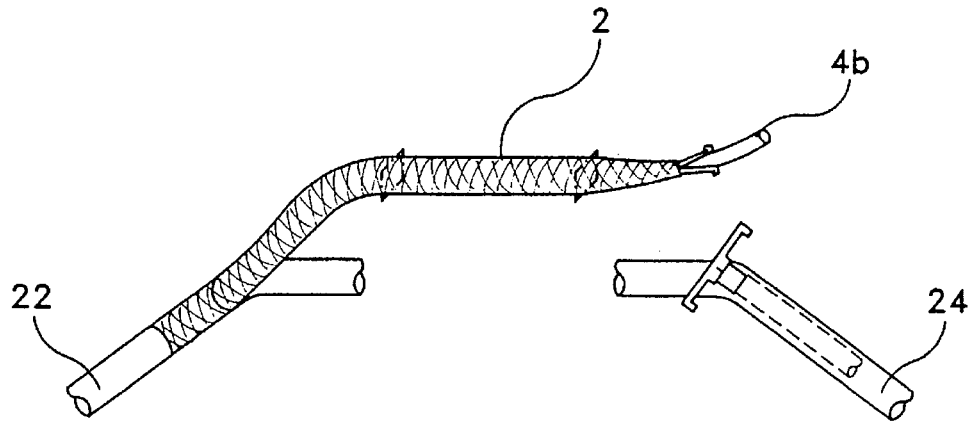
Figure 4H:
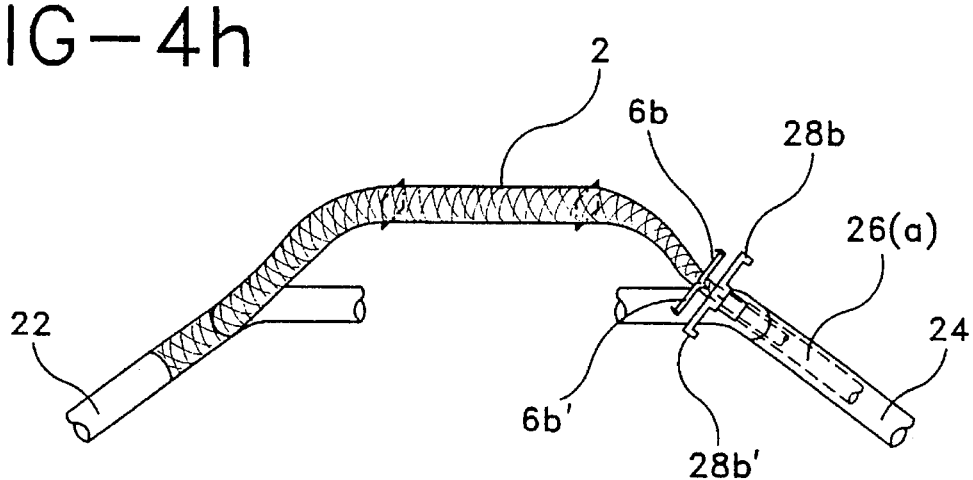
Figure 4I:
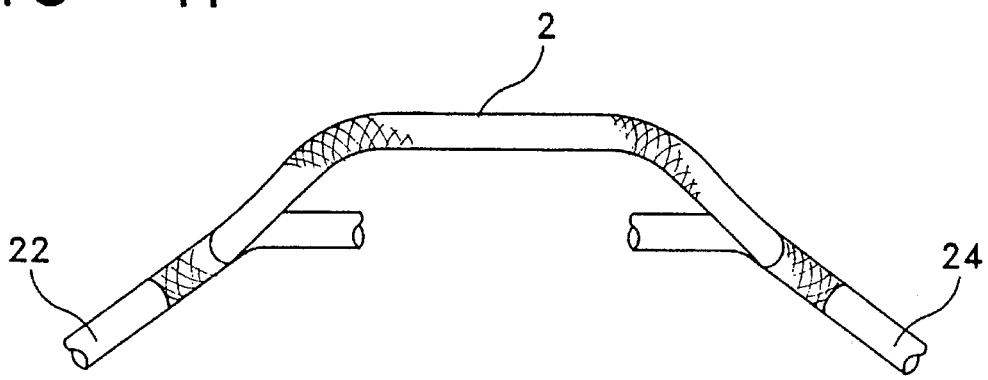

Removable retaining element 4, vascular access means 26a,b (FIGS. 4(a)–4(i)), gripping means 14a,b (FIG. 2), and tunnel means 34 (FIGS. 4(b)–4(d)) will be made from suitable materials, generally polymeric materials such as PTFE, FEP or polyethylene.

Figure 5A:
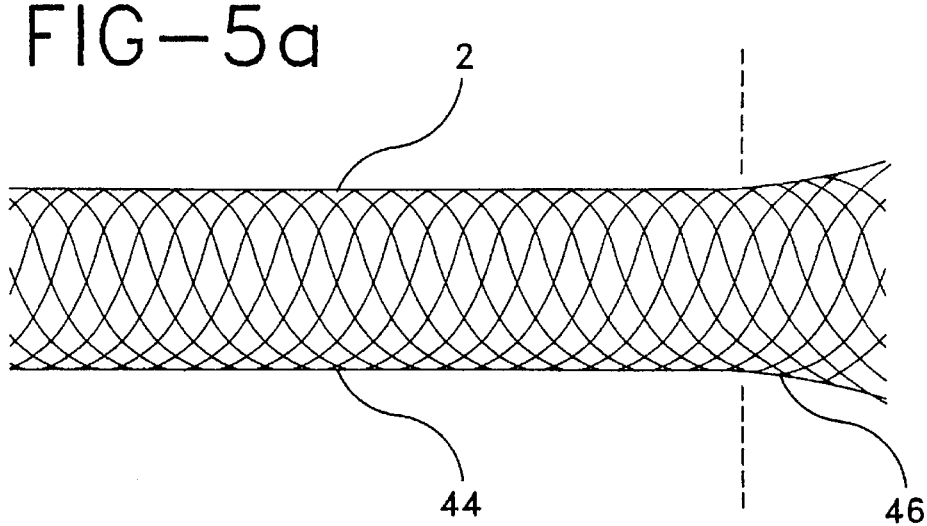
FIGS. 5(a)–5(c) are side elevational views of three embodiments of the body implantable device of the present invention.
Figure 5B:
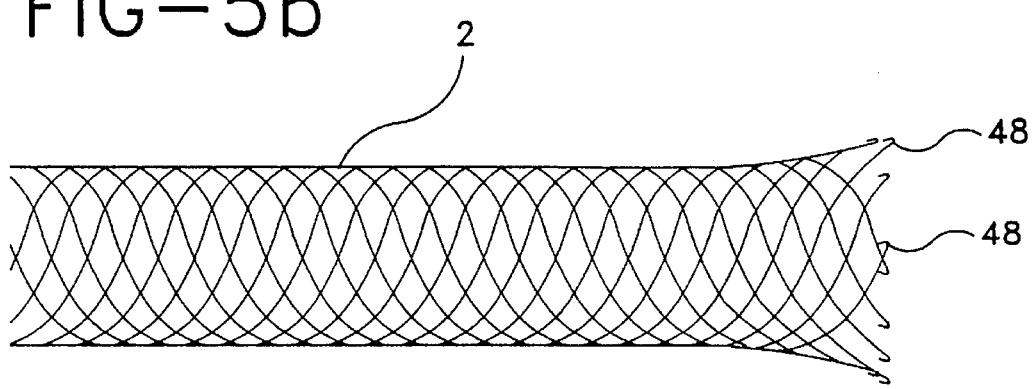
Figure 5C:
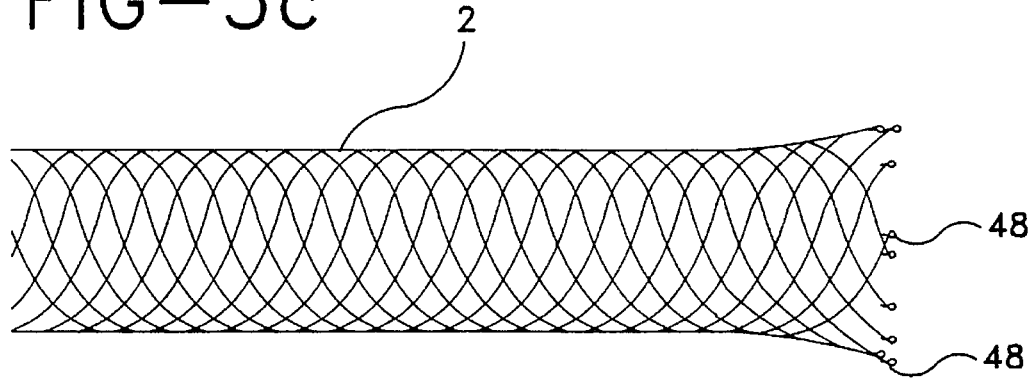
Figure 6:
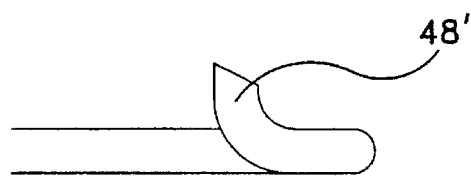
FIG. 6 is a side view of an anchoring means of the present invention.

FIGS. 5(a)–5(c) illustrate alternative embodiments of the stent-graft of the present invention. In some cases the outer elastic layer will extend along the entire length of the wire mesh (not shown). It is preferable, however, to configure the stent graft so that it becomes anchored or fixed at each end inside of the vessel segments in which it is inserted. Thus, FIG. 5(a) illustrates an embodiment where the outer flexible layer does not extend the full length of the wire mesh, creating a covered segment 44 and an uncovered segment 46 to the right of the dashed line which is exposed and more capable of "grabbing" the inside of the vascular lumen. In FIGS. 5(b) and 5(c) the ends of the wire mesh filaments are configured with barbs 48 to grab onto the inside of the vascular lumen. An alternative barb 48' is illustrated in FIG. 6. Such configurations enable the stent-graft to create a suitable seal with the inside of the vascular lumen, avoiding the need for sutures. In certain applications, however, sutures may be used to create a firmer seal.

Figure 7A:
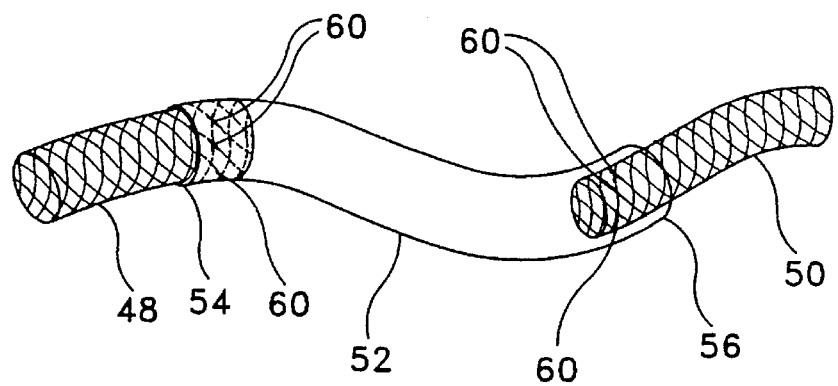
FIGS. 7(a)–7(b) are side elevational views of alternative stent-grafts of the present invention.
Figure 7B:
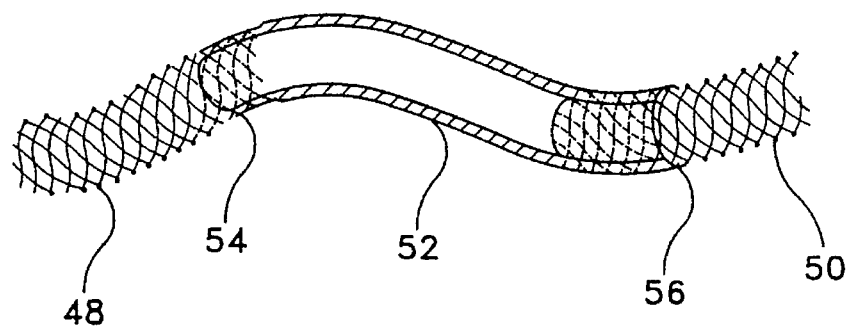

FIGS. 7(a) and 7(b) show alternative stent-grafts of the present invention. FIG. 7(a) shows a first stent 48 and a second stent 50, separated by a tubular elastic layer 52. The elastic layer has a first end 54 and a second end 56, each configured along the length of the respective stent. The stents 48,50 are attached to the elastic layer 52 by sutures 60. It is preferable for elastic layer 52 to at least partially cover stents 48,50, but in certain embodiments it will be configured so that the elastic layer 52 abuts the ends of the stents 48, 50, and the elastic layer is attached to the stents by some means such as by sutures. FIG. 7(b) shows an embodiment wherein elastic layer 52 embeds the filaments making up segments of the first stent 48 and the second stent 50. Sutures are not required in this particular embodiment.

Figure 8:
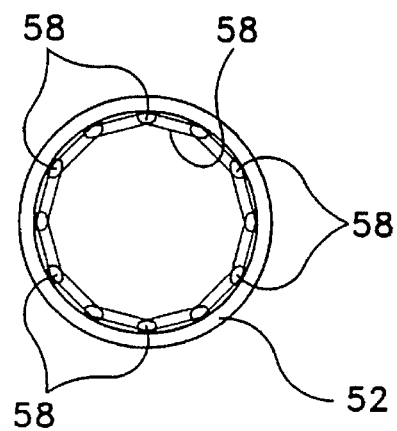
FIG. 8 is a top view of an alternative stent-graft of the present invention.

FIG. 8 shows a top view of a stent graft of the present invention. In this embodiment, elastic layer 52 is configured outside of the filaments 58 making up the stents. In other embodiments, the elastic layer will be configured inside of the filaments, or will embed the filaments.

Figure 9A:
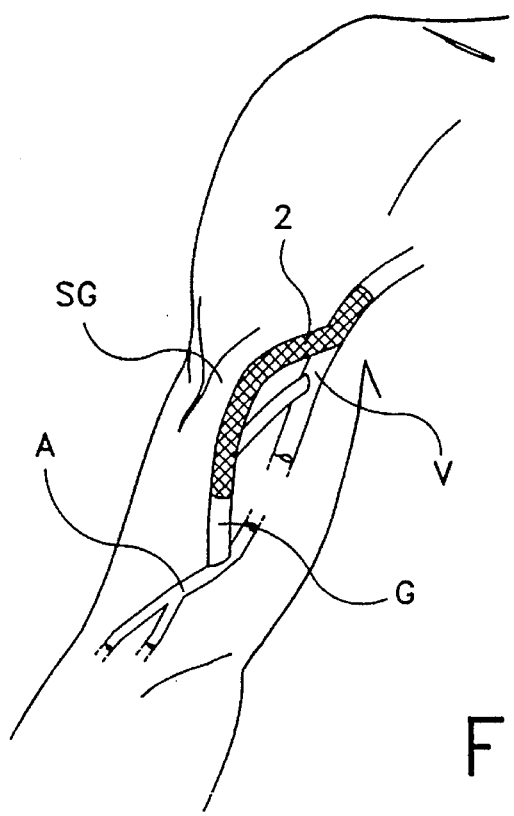
FIGS. 9(a)–9(c) show three configurations of the stent-graft of the present invention inside human anatomy.
Figure 9B:
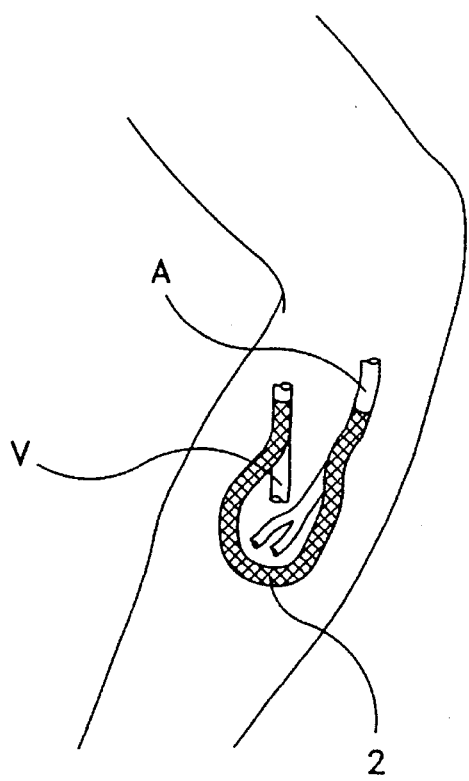
Figure 9C:
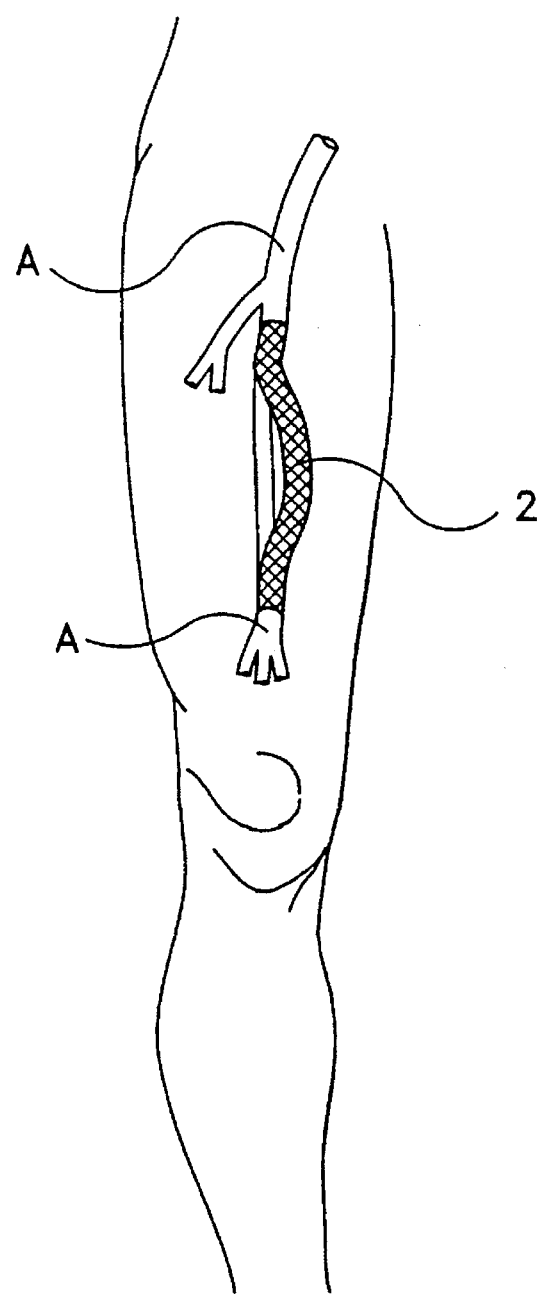

FIGS. 9(a)–9(c) illustrate the present invention after stent-graft deployment in the body. FIG. 9(a) shows stent-graft revision of a brachial artery-axillary vein. FIG. 9(b) shows stent-grafting of an arteriovenous forearm loop. FIG. 9(c) shows stent-grafting of an occluded femoral artery.

Figure 10:
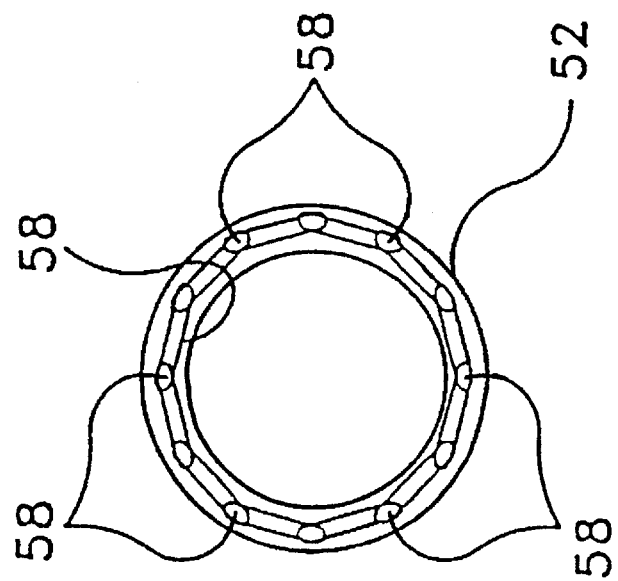
FIG. 10 is a top view of an alternative stent-graft of the present invention.

FIG. 10 shows a top view of a stent graft of the present invention. In this embodiment, elastic layer 52 is configured to embed the filaments 58 making up the stents. As noted above, this embedding may extend along the entire length of the stent or merely along a selected portion thereof.

EXAMPLE

An acute, non survival study was performed utilizing 10 adult mongrel dogs. All procedures were performed under general anesthesia (pentobarbital, titrated to effect). The animals were incubated and mechanically ventilated. For diagnostic arteriographic purposes, a 6 French sheath was placed in the left carotid artery by cutdown. In all but 1 dog, both groins were shaved. In the remaining dog the right neck was shaved. No anticoagulants were given.

A) Device

In all but 1 animal, 6 millimeter diameter silicone covered Wallstents were used ranging in length from 12 to 18 centimeters. In 1 animal, an 8 millimeter diameter silicone covered Wallstent was used. The stent-grafts were made by Schneider (USA) Inc, Minneapolis, Minn. The stent-grafts were constrained at either end by a segment of 8 French peel-away sheath.

B) Procedure

In 1 animal a straight 8 millimeter graft was created semipercutaneously between the right common carotid artery and right external jugular vein. The right common carotid artery was exposed by cutdown and accessed with a micropuncture set (Cook, Inc., Bloomington, Ind.). After exchanging for a 0.035 inch wire, the arteriotomy was dilated to 10 French and a 10 French peel-away sheath (B. Braun Medical Inc., Bethlehem, Pa.) was inserted. Next, percutaneous puncture of the right external jugular vein was performed in a retrograde fashion using the micropuncture set. This access was also dilated to 10 French over a 0.035 inch wire. A 10 French peel-away sheath was inserted. Next, the dilator of the arterial peel-away sheath was removed and the arterial end of the graft (enclosed in its own segment of peel-away sheath) passed through the sheath. The outer peel-away sheath was then removed followed by the inner peel-away sheath which resulted in deployment of the stent-graft within the vessel. Hemostasis was maintained by pinching the graft. Next, the venous end of the graft (enclosed in its segment of peel-away sheath) was passed through the venous sheath and deployed in similar fashion to the arterial end of the graft. After placement of the second "anastomosis", arteriography was performed to demonstrate patency of the shunt.

The remaining 10 grafts in nine animals were placed in femoral loop fashion from the common femoral artery to the common femoral vein. For this procedure, a dermatotomy or short skin incision ranging from 0.5 to 4 centimeters was made just below the inguinal ligament. The vessels were not dissected free. This incision only served to enable creation of a subcutaneous pocket and to make insertion of the ends of the stent graft through the peel-away sheaths easier. A 5 mm counterincision was made approximately 8 centimeters distal to the original incision. Using a hemostat, the pocket for the femoral loop was created by blunt dissection from the counterincision toward the femoral incision/dermatotomy. A short (30 mm) 0.035 inch guide wire was pulled through each limb of the loop and left in place. Next, access was gained to the right common femoral artery and vein using a micropuncture set. After exchanging for a 0.035 inch guide wire, the arteriotomy and venotomy were dilated and 10 French peel-away sheaths inserted. Next, an 18 French peel-away sheath was placed over each guide wire within the subcutaneous pocket and a 6 millimeter in diameter, 12–18 centimeter stent-graft was passed through each peel-away sheath in order to form a femoral loop (the length of the graft used was based on the available devices, the tunnel length was adjusted accordingly). A cap was placed on the venous end of the graft to promote hemostasis during graft insertion. Once the graft was in place in the tunnel, the arterial end of the graft was placed through the 10 French peel-away sheath into the common femoral artery. The outer peel-away sheath was removed followed by the retaining peel-away sheath on the graft which resulted in deployment of the arterial end of the graft. Next, the venous end of the graft was pinched to promote hemostasis and the cap removed. It was then placed through the venous sheath and deployed in similar fashion to the arterial end. One modification of this technique that was found helpful was to have a 5 French Fogarty catheter in the right external iliac artery which was inflated just prior to placement of the graft and kept inflated during the 1 to 2 minutes that it took to deploy the graft. It was then deflated. This technique resulted in significantly better hemostasis, but it is not necessary.

After placement of the venous end of the graft, it was palpated to confirm the presence of a thrill. Arteriography was then performed using a catheter placed via the left carotid sheath into the ipsilateral external iliac artery. Arteriography was recorded using cut film or 105 millimeter spot film technique.

The animals were then kept alive but under anesthesia for up to 6 ½ hours (range 1–6.5 hours, mean 4.1 hours). At the end of this time, repeat arteriography was performed to confirm continued patency of the graft. Repeat palpation was also performed. No anticoagulants were given during this time or during any other portion of the procedure. In 2 animals, the procedure was carried out under sterile technique in anticipation of a survival experiment. The graft placement procedure was identical to that in the acute animals.

At the completion of the experiment, the animals were killed with an overdose of pentobarbital. The stents were excised and examined grossly for any evidence of thrombosis or any other abnormality.

C) Results 10 successful percutaneous shunt placements and 1 semi-percutaneous placement were achieved. All femoral loop grafts developed a palpable thrill immediately after creation which was maintained for the duration of the experiment. The neck graft (our first graft) initially had a small amount of thrombus within it which was dislodged with a catheter via the femoral approach. After dislodgement of this clot there was a palpable thrill in the graft. None of the femoral grafts developed thrombus at any time during the procedure; this was confirmed by visual inspection after graft removal. No "anastomotic" leaks were observed at any time during the experiment. Small leaks in the silicone coating occurred in four grafts, in three of these hemostasis was achieved with gentle pressure. In one graft, continued leaking resulted in development of a hematoma and graft dislodgement at 1 hour post placement. None of the leaks were visible angiographically. Fistulography in the femoral loops demonstrated widely patent grafts immediately after placement and just prior to sacrifice at 2.5–6.5 hours post placement; in three grafts delayed fistulography was not performed due to premature dislodgement. The single neck graft fistulogram initially showed some clot but after clot dislodgement was widely patent and remained patent at 2 hours post placement (just prior to sacrifice).

Both attempted survival experiments were unsuccessful due to shunt dislodgement. Prior to attempting survival experiments, the hindlimbs of the acute animals had been extensively manipulated showing good stability of the shunts; therefore it was felt that dislodgement would not occur in a conscious animal. However, in one animal, 1.5 hours after creation of the shunt, a large hematoma developed in the groin containing the shunt while lifting the dog to transfer it to its cage. The shunt was confirmed fluoroscopically to be dislodged and the animal sacrificed. The second animal was transferred to its cage without lifting by the legs; however, as the animal awoke from anesthesia, repeated kicking apparently dislodged the shunt (3.5 hours after insertion) and the animal developed a large hematoma in the groin. The shunt was confirmed fluoroscopically to be dislodged and the animal sacrificed.

One skilled in the art will appreciate that the foregoing figures, embodiments, and example are presented for purposes of illustration and not for limitation. Alternative embodiments will become apparent to one skilled in the art. For instance, the stent-graft of the present invention may have two biaxially configured stents sandwiching an elastic layer. Three stents may be used in various configurations. These and other variations are within the purview of the present invention.

We claim:

1. An apparatus comprising:
   a body implantable self-expanding stent comprising a flexible tube of open weave construction having a first end and a second end, the ends being compressible into radially compressed states, the flexible tube having an elastic layer arranged along at least a portion of its length; and
   first and second removable retaining elements secured to the flexible tube proximate the first and second ends, respectively, for maintaining the first and second ends of the self-expanding stent in radially compressed states until removed, wherein each retaining element is a peel-away sheath adapted for insertion into vascular access means, said peel-away sheath comprising a tubular material attached to at least two leaves, the leaves upon an application of force being adapted to tear the tubular material thereby separating the sheath into removable pieces allowing the stent to self-expand.

2. The apparatus of claim 1 wherein the leaves comprise handles to facilitate the application of the force.

3. The apparatus of claim 1 wherein the flexible tube is constructed of helical, braided strands of biocompatible material.

4. The device of claim 3 wherein the biocompatible material is selected from the group consisting of stainless steel, Elgiloy, Nitinol, and combinations thereof.

5. The device of claim 3 wherein the biocompatible material is a plastic.

6. The apparatus of claim 1 wherein the elastic layer at least partially embeds the flexible tube.

7. The apparatus of claim 1 wherein the elastic layer comprises a semi-permeable biostable material selected from the group consisting of polytetrafluoroethylene, polyester, polyurethane, and silicone.

8. The apparatus of claim 1 and further, including at least one gripping means disposed along at least a portion of the length of the flexible tube between the first and second removable retaining elements for protecting the flexible tube member.

9. The apparatus of claim 8 and further, wherein said gripping means comprises a peel-away sheath.

10. The apparatus of claim 9 and further, including a cap member for selective placement over one of the first and second ends of the flexible tube to inhibit the flow of fluid therethrough.

11. A system for delivering a percutaneous stent-graft, the system comprising:
   a) a body implantable self-expanding stent comprising a flexible tube member of open weave construction having a first end and a second end, the ends being compressible into radially compressed states, the flexible tube having an elastic layer disposed along at least a portion of its length;
   b) first and second removable retaining elements secured to the flexible tube proximate the first and second ends, respectively, for maintaining the first and second ends of the self-expanding stent in radially compressed states wherein the retaining elements comprise peel-away sheaths adapted for insertion into vascular access means; and
   c) first and second vascular access means adapted to receive the first and second removable retaining elements, respectively, wherein the first and second vascular access means comprise peel-away sheaths.

12. The system of claim 11 wherein the peel-away sheaths comprise a tubular material attached to at least two leaves, the leaves upon an application of force being adapted to tear the tubular material thereby separating the sheath into removable pieces.

13. The system of claim 12 wherein the leaves comprise handles to facilitate the application of the force.

14. The apparatus of claim 11 and further, including at least one gripping means disposed along at least a portion of the length of the flexible tube member between the first and second removable retaining elements for protecting the flexible tube member.

15. The apparatus of claim 14 and further, wherein said gripping means comprises a peel-away sheath.

16. The apparatus of claim 15 and further, including a cap member for selective placement over one of the first and second ends of the flexible tube member to inhibit the flow of fluid therethrough.

17. A system for delivering a percutaneous stent-graft, comprising:
   a) a body implantable self-expanding stent comprising a flexible tube member of open weave construction having a first end and a second end, the ends being compressible into radially compressed states, the flexible tube having an elastic layer disposed along at least a portion of its length;
   b) first and second removable retaining elements secured to the flexible tube proximate the first and second ends, respectively, for maintaining the first and second ends of the self-expanding stent in radially compressed states, wherein the retaining elements comprise peel-away sheaths adapted for insertion into vascular access means;
   c) at least one gripping means disposed along at least a portion of the length of the flexible tube member between the first and second removable retaining elements for protecting the flexible tube member.

* * * * *